United States Patent [19]

Leonardi

[11] Patent Number: 4,688,272

[45] Date of Patent: Aug. 25, 1987

[54] SPORTS FRAME WITH RESILIENT PADS

[75] Inventor: Peter F. Leonardi, Gloversville, N.Y.

[73] Assignee: Halo Optical Products, Inc., Johnstown, N.Y.

[21] Appl. No.: 721,634

[22] Filed: Apr. 9, 1985

[51] Int. Cl.[4] .............................................. A61F 9/02
[52] U.S. Cl. ........................................... 2/431; 2/442; 2/446; 2/449; 351/87; 351/132
[58] Field of Search .................. 2/431, 426, 439, 440, 2/441, 442, 443, 445, 446, 448, 449; 351/138, 136, 131, 87, 88, 139, 132

[56] References Cited

U.S. PATENT DOCUMENTS

| | | | |
|---|---|---|---|
| 1,306,357 | 6/1919 | Shindel | 2/439 |
| 1,310,119 | 7/1919 | Harper | 2/452 X |
| 1,949,595 | 3/1934 | Willson et al. | 2/14 |
| 2,435,653 | 2/1948 | Maurer | 128/141 |
| 2,513,507 | 7/1950 | Moeller | 2/450 |
| 2,545,428 | 3/1951 | Liautaud | 2/452 |
| 2,561,402 | 7/1951 | Nelson | 2/448 X |
| 2,598,265 | 5/1952 | Jones | 2/14 |
| 2,642,568 | 6/1953 | Stewart | 2/14 |
| 2,688,135 | 9/1954 | Stegeman | 2/14 |
| 2,706,815 | 4/1955 | Parmelee | 2/439 |
| 2,903,700 | 9/1959 | Finken | 2/10 |
| 3,000,011 | 9/1961 | Sterne et al. | 2/14 |
| 3,336,599 | 8/1967 | Gatti et al. | 2/14 |
| 3,345,121 | 10/1967 | De Angelis | 2/446 X |
| 3,565,517 | 2/1971 | Gitlin et al. | 351/138 X |
| 3,663,959 | 5/1972 | Loubeyre | 2/14 N |
| 4,087,865 | 5/1978 | Garofalo | 2/428 |
| 4,142,784 | 3/1979 | Bononi | 351/87 X |
| 4,176,410 | 12/1979 | Matthias | 2/436 |
| 4,229,837 | 10/1980 | Solari | 2/439 |
| 4,279,040 | 7/1981 | Garafalo | 2/428 |
| 4,367,561 | 1/1983 | Solari | 2/439 |
| 4,405,214 | 9/1983 | Bolle | 351/138 X |
| 4,425,669 | 1/1984 | Grendol | 2/436 |

FOREIGN PATENT DOCUMENTS 0144718 11/1980 German Democratic Rep. ........................ 351/132
626488 7/1949 United Kingdom .

*Primary Examiner*—Peter Nerbun
*Attorney, Agent, or Firm*—Roylance, Abrams, Berdo

[57] ABSTRACT

A sports eyewear frame having resilient padding attached to the frame by means of one or more tongues which are attached to the pads, and interlocked in openings provided in the frame. The pads, which can be molded-on or snapped-on, provide the sports frame with lifetime padding under normal wear and tear conditions.

4 Claims, 7 Drawing Figures

SPORTS FRAME WITH RESILIENT PADS

FIELD OF THE INVENTION

The present invention relates to safety sports eyewear. More particularly, this invention relates to sports eyewear frames for use in sporting activities to prevent eye injury to a player from a ball, equipment, hands, or the like.

BACKGROUND OF THE INVENTION

In a large number of sporting activities, such as tennis, handball, squash, racquetball, basketball, soccer, and other sporting activities in which there is fast movement of players and the use of a ball, there is a continuing danger of a participant being struck in the eye by the ball, racket or hand of an opponent, which can result in severe injury or even, in some cases, loss of an eye. Thus, the use of protective eyewear is advisable.

Numerous types of safety sports eyewear are available, as exemplified by U.S. Pat. Nos. 4,367,561, and 4,229,837 to Solari; and U.S. Pat. No. 4,176,410 to Matthias.

Many of these sports frames have padding in the nose, forehead, and temple areas which make the eyewear safer and more comfortable for the participant. In most cases, however, the padding which is secured to the frame by adhesive detaches from the frame in a short time. This is partly because of the normal wear and tear, and partly because of moisture from the participant's perspiration.

Thus, there is a continuing need for a sports frame having padding which will not become detached from the frame even after extended wear.

SUMMARY OF THE INVENTION

Accordingly, the primary object of the present invention is to provide a sports frame which has padding that will not become detached from the frame even after extended wear and use.

The foregoing object is basically attained by providing a sports frame with at least one resilient pad comprising a rigid frame having first and second sides, at least one opening formed in the frame extending from the first side to the second side, and at least one resilient pad which has a tongue that is interlocked in the frame opening.

Other objects, advantages, and salient features of the present invention will become apparent from the following detailed description, which, taken in conjunction with the annexed drawings, discloses preferred embodiments of the invention.

DRAWINGS

Referring now to the drawings which form a part of this original disclosure:

DETAILED DESCRIPTION OF THE INVENTION

Figure 1:
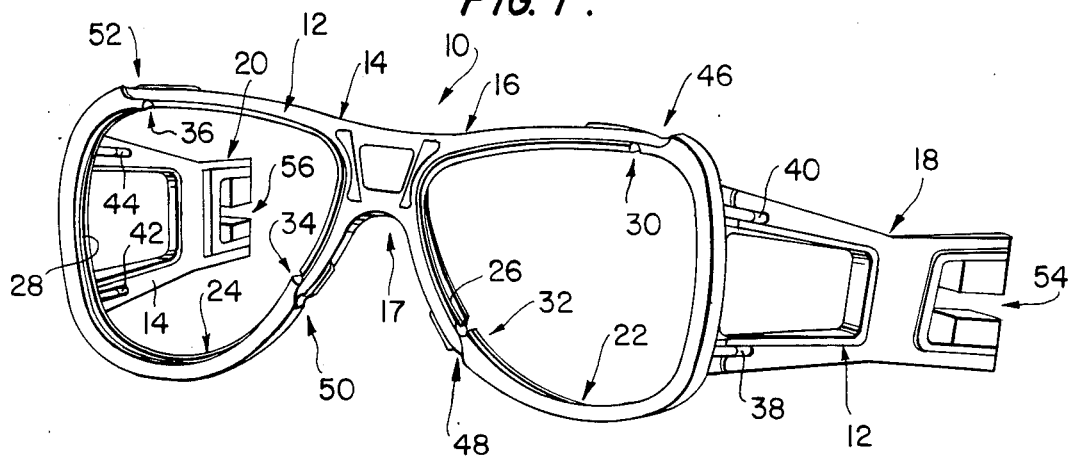
FIG. 1 is a front perspective view of a sports frame having several openings therein in accordance with the present invention.

As seen in FIG. 1, a sports frame 10 in accordance with the invention may take the form of an integrally molded, rigid frame having first and second sides 12 and 14, and including front portion 16 having a nose-area recess 17, and rearwardly extending side portions 18 and 20 connected thereto. The front portion 16 has two apertures therein 22 and 24 having inwardly opening peripheral recesses 26 and 28 therein which are designed to receive lenses that may be either refractive or non-refractive.

The front portion 16 of sports frame 10 has openings 30, 32, 34, and 36 which extend from the first side 12 to the second side 14 of the front portion 16. The side portions 18 and 20 also contain openings 38, 40, 42, and 44 which likewise, extend from the first side 12 to the second side 14 of the side portions 18 and 20. The front portion 16 of frame 10 also contains openings 46, 48, 50, and 52 extending from side to side.

As seen in FIG. 1, openings 30, 32, 34, and 36, as well as openings 46, 48, 50 and 52, comprise through-slots which extend from side to side of the frame 10, while openings 38, 40, 42, and 44 comprise through-apertures which extend from side to side of the frame.

The side portions 18 and 20, in the form of rearwardly extending members, contain additional openings 54 and 56, which are designed to receive retaining means for retaining the sports frame securely against the face of the wearer. The retaining means commonly comprises an elastic headband.

Figure 2:
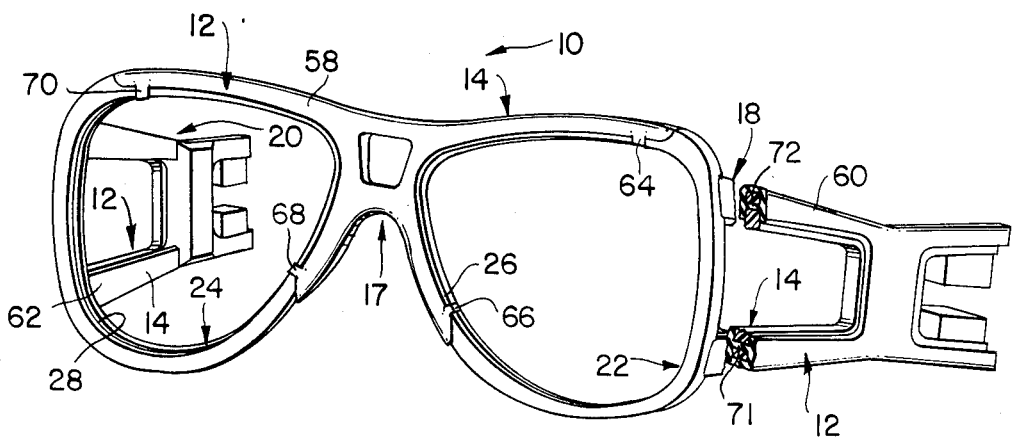
FIG. 2 is a front perspective view of the sports frame of FIG. 1 after padding has been molded onto the frame.

FIG. 2 shows the sports frame of FIG. 1 after resilient pads 58, 60 and 62 have been molded thereto. As seen in FIG. 2, slots 30, 32, 34, and 36 now contain tongues 64, 66, 68, and 70 which are interlocked in these slots by being attached to the resilient nose-area padding 58 on the first side 12 of sports frame 10, extending longitudinally through the slots and being attached to the padding 58 on the second side 14 of the frame. Similar tongues, not shown, are provided in slots 46, 48, 50 and 52.

As seen in FIG. 2, tongues 71 and 72 also extend from the padding 60 on the first side 12 through apertures 38 and 40 and are attached to the padding on the second side 14, thereby interlocking the tongues in the apertures and securing the temple-area padding to the side portion 18. Likewise, tongues extend from the padding 62 on the first side 12 of side portion 20 through apertures 42 and 44, and are attached to the padding on the second side 14, thereby securing the temple-area padding on the side portion 20.

The integrally molded frame 10 can be comprised of any material, but is advantageously comprised of a lightweight, moldable, shatterproof polymeric material, such as cellulose acetate.

The padding can also be comprised of any material which provides a cushioning effect for the wearer, and which is resilient, able to withstand normal wear and tear, and able to be molded onto the frame. A particularly advantageous padding which fulfills all of the above requirements is Kraton G, a proprietary product of Shell Chemical Co. which is comprised of a block copolymer of butadiene, isoprene, and styrene.

The process for making the padded sports frame shown in FIGS. 1-2 is relatively simple and straightforward. First, the frame is molded out of a polymeric material such as, for example, cellulose acetate. The frame is then removed from the first mold and placed in a second mold where the padding is molded around the frame and through the openings, thereby assuring the permanency of the pad.

EMBODIMENT OF FIGS. 3-7

Referring now to FIGS. 3-7, an alternate embodiment of the invention is shown comprising a frame 80 having first and second sides 82 and 84, and apertures 86 and 88 having peripheral recesses 90 and 92 therein for receiving lenses that are either refractive or non-refractive.

Figure 3:
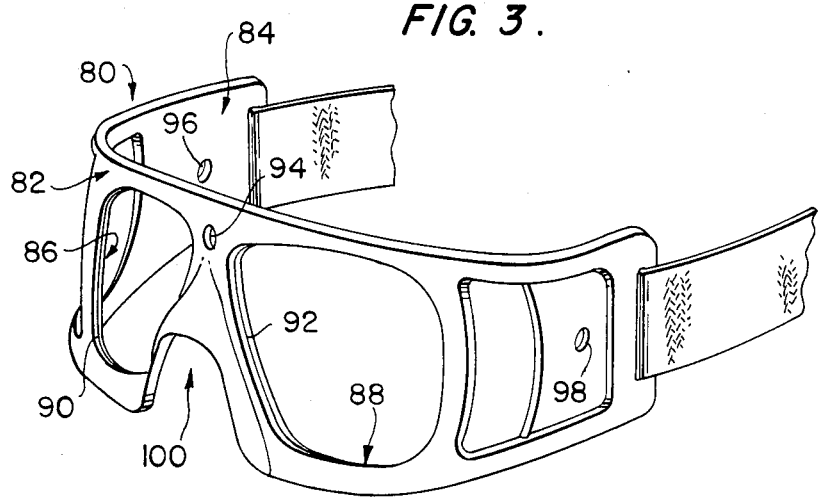
FIG. 3 is a right side perspective view of a different sports frame having openings therein in accordance with the invention.

Also shown in FIG. 3 are openings 94, 96, and 98 which extend from the first side 82 to the second side 84 of frame 80. A nose recess 100 is also provided.

Figure 4:
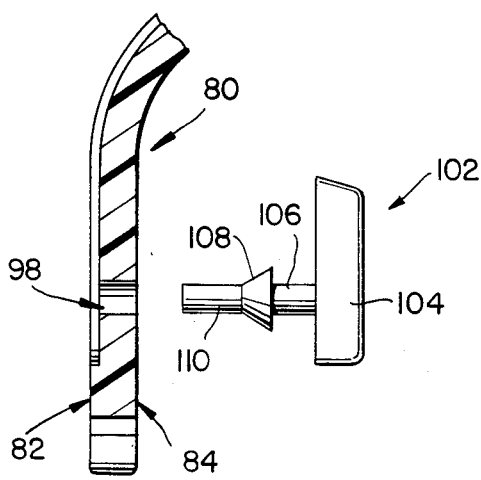
FIG. 4 is a top plan view in section of the sports frame of FIG. 3 taken along line 4—4, and padding having a tongue which is to be interlocked in the opening of the sports frame.
Figure 5:
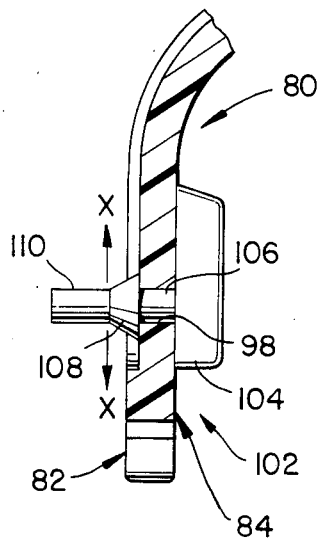
FIG. 5 is a top plan view in section of the sports frame and padding of FIG. 4 showing the tongue of the padding interlocked in the opening of the sports frame.

Referring now to FIGS. 4 and 5, the method by which modified resilient pads are attached to frame 80 is illustrated.

As seen in FIG. 4, temple-area resilient pad 102 is shown having a base portion 104, cylindrical tongue 106, enlarged frustoconical portion 108 and elongated cylindrical segment 110, all of which are integrally formed as one piece. Adjacent the pad 102 is opening 98 of sports frame 80, which is shown in FIG. 3.

In order to secure the pad 102 to frame 80 and interlock the tongue in the opening 98, elongated segment 110 is inserted through the opening 98 on the second side 84 of frame 80 until it protrudes through the opening on the first side 82. The elongated segment 110 is then pulled through the opening until the enlarged portion 108 is located entirely on the first side of the frame as shown in FIG. 5. Because the tongue 106 is approximately the same length as the length of the opening 98, the base 104 is held securely against the second side of the frame 84.

Once the pad 102 is secured to the frame 80, the elongated segment 110 may be removed by cutting along line x—x, thereby leaving only the enlarged portion 108 remaining on the first side 82 of frame 80.

Figure 6:
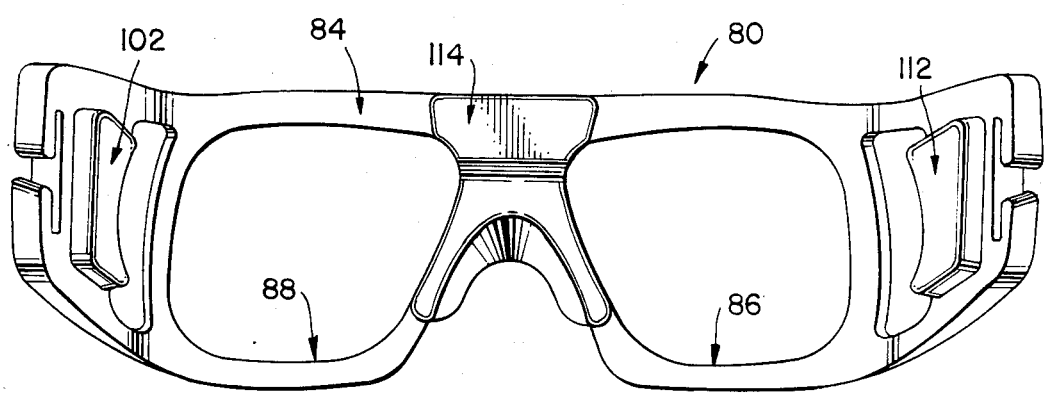
FIG. 6 is a rear perspective view of the sports frame of FIG. 3 after the nose pad and temple pads have been attached.
Figure 7:
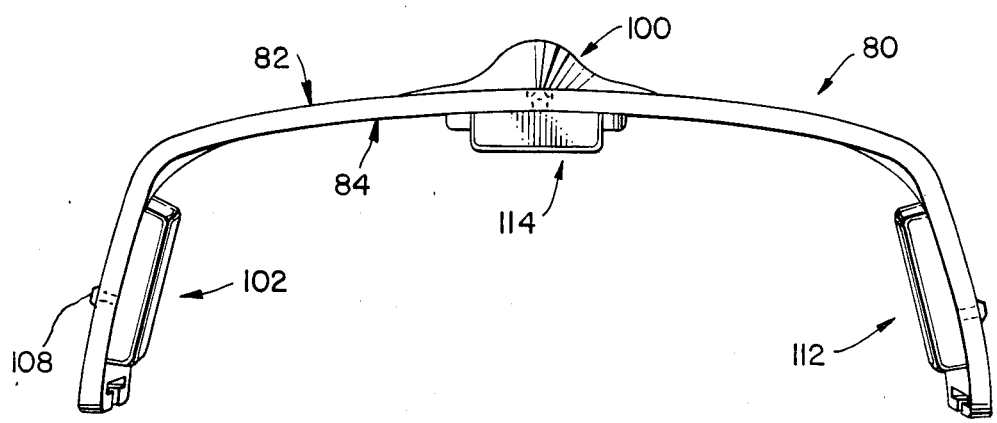
FIG. 7 is a top plan view of the sports frame of FIG. 6 showing the positioning of the padding, the frame openings, and the interlocked tongues.

FIGS. 6 and 7 show the sports frame after the temple pads 102 and 112, and nose and forehead pad 114 have been secured in the manner described above.

While two advantageous embodiments have been chosen to illustrate the invention, it will be understood by those skilled in the art that various changes and modifications can be made therein without departing from the scope of the invention as defined in the appended claims.

What is claimed is:

1. A sports frame for eye protection, comprising:
   a rigid frame having first and second sides, and having two apertures for receiving lenses;
   slots in said frame opening at axial ends thereof on said first and second sides and opening laterally along entire lengths thereof into said apertures; and
   resilient padding molded to said frame adjacent said apertures, said padding having tongues extending through said slots securing said padding to said frame, said tongues having surfaces generally conforming to and defining portions of said apertures.

2. A sports frame according to claim 1 wherein said frame comprises a recess for receiving a nose of a wearer, two of said slots being located adjacent an open end of said recess securing padding extending through said recess and terminating adjacent said open end.

3. A sports frame according to claim 2 wherein said padding extends along a top portion of said frame, two of said slots being located adjacent ends of said padding on said top portion.

4. A sports frame according to claim 3 wherein said frame has rearwardly extending members for protecting temples of a wearer, said rearwardly extending members having through bores securing padding molded thereon.

* * * * *